United States Patent [19]

Newman

[11] Patent Number: 4,833,162

[45] Date of Patent: May 23, 1989

[54] SUBSTITUTED BENZENEACETONITRILES AND THEIR USE AS CALCIUM CHANNEL BLOCKERS

[75] Inventor: Howard Newman, Monsey, N.Y.

[73] Assignee: American Cyanamid Company, Stamford, Conn.

[21] Appl. No.: 151,725

[22] Filed: Feb. 3, 1988

[51] Int. Cl.⁴ ........................ A61K 31/08; C07C 43/02
[52] U.S. Cl. ...................................... 514/523; 558/390
[58] Field of Search ......................... 558/390; 514/523

[56] References Cited

U.S. PATENT DOCUMENTS 3,261,859  7/1966  Dengel .................................. 558/390

Primary Examiner—Mary C. Lee
Assistant Examiner—J. Richter
Attorney, Agent, or Firm—Alan M. Gordon

[57] ABSTRACT

This invention relates to novel A-[[2-[[2-(3,4-dimethoxyphenyl)ethyl]methylamino]ethyl]thio]-3,4-dimethoxy-A-substituted benzeneacetonitrile compounds and a process for the preparation of said compounds. The compounds are useful as calcium channel blocking agents.

6 Claims, No Drawings

SUBSTITUTED BENZENEACETONITRILES AND THEIR USE AS CALCIUM CHANNEL BLOCKERS

SUMMARY OF THE INVENTION

This invention is concerned with a new group of compounds, namely A-[[2-[[2-(3,4-dimethoxyphenyl)ethyl]methylamino]ethyl]thio]-3,4-dimethoxy-A-substituted benzeneacetonitriles, having the structure

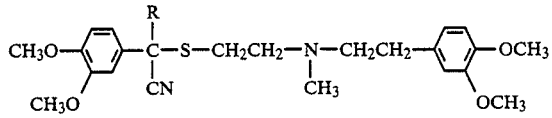

wherein R is hydrogen, $C_{1-6}$ alkyl or aryl, and pharmaceutically acceptable salts thereof. This invention is also concerned with processes for the synthesis of the novel group of compounds.

These new compounds are pharmacologically active cardiac agents, having utility as calcium channel blockers.

BACKGROUND OF THE INVENTION

The calcium channel blocker class of compounds act by inhibiting the movement of calcium ions into membrane pores of vascular smooth and cardiac muscle cells. Such compounds have use in treating angina pectoris and supraventricular arrhythmias.

The novel compounds of the present invention are related to Verapamil, a known cardiac drug with calcium channel blocking activity. Verapamil has the Chemical Abstracts name A-[3-[[2-(3,4-dimethoxyphenyl)ethyl]methylamino]propyl]-3,4-dimethoxy-A-(1-methylethyl) benzeneacetonitrile and has the structure

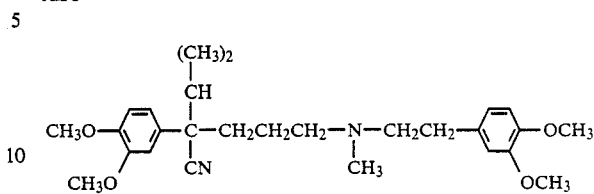

Verapamil is described in U.S. Pat. No. 3,261,859 and is sold as a calcium channel blocker under a variety of trade names.

DETAILED DESCRIPTION OF THE INVENTION

The A-[[2-[[2-(3,4-dimethoxyphenyl)ethyl]methylamino]ethyl]thio]-3,4-dimethoxy-A-substituted benzoneacetonitrile compounds of this invention are benzeneacetonitriles substituted with hydrogen, $C_{1-6}$ lower alkyl or aryl groups. Preferred substituents are hydrogen and 1-methylethyl. The 1-methylethyl substituent is particularly preferred, so that the preferred compound is named A-[[2-[[2-(3,4-dimethoxyphenyl)ethyl]methylamino]ethyl]thio]-3,4-dimethoxy-A-(1-methylethyl) benzeneacetonitrile.

The A-[[2-[[2-(3,4-dimethoxyphenyl)ethyl]methylamino]ethyl]thio]-3,4-dimethoxy-substituted benzeneacetonitrile group of compounds may be prepared according to the following reaction scheme.

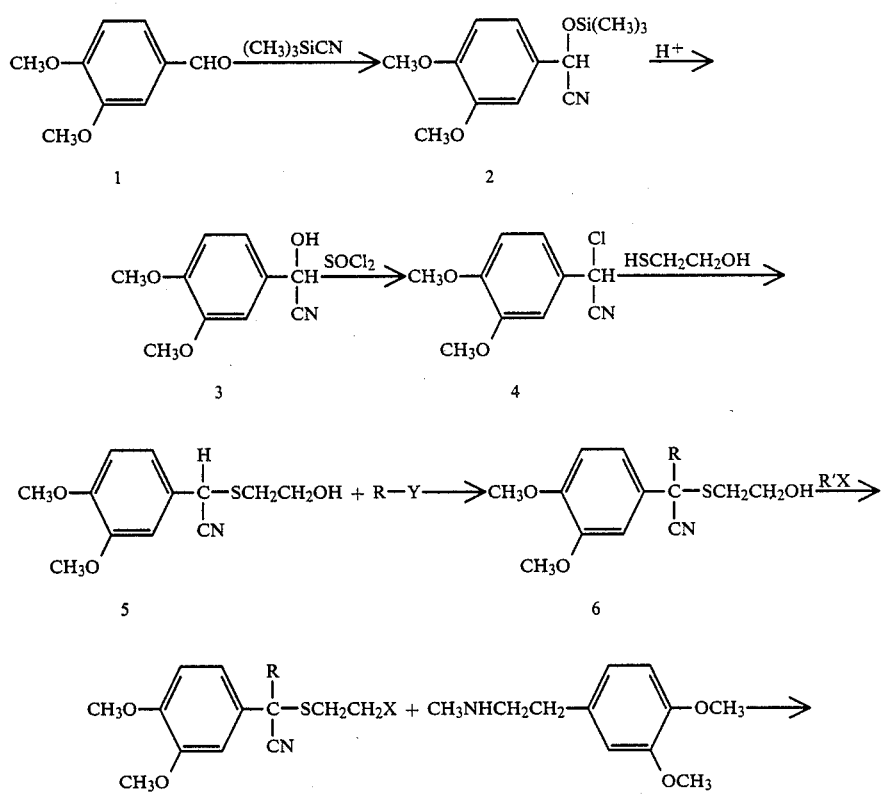

-continued

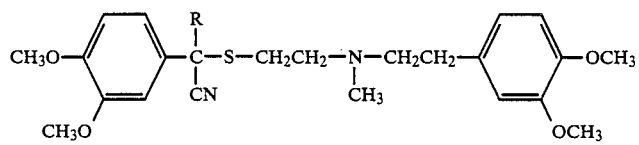

8

In accordance with the above reaction scheme, 3,4-dimethoxybenzaldehyde 1 and trimethylsilylcyanide in dichloromethane are reacted in the presence of zinc iodide giving 2, which is then reacted with a dilute acid giving 3, which is then reacted with thionyl chloride in dichloromethane, giving 3,4-dimethoxyphenyl-A-chloroacetonitrile 4. Compound 4, in methanol, is then reacted with a solution of 2-mercaptoethanol in 1M methanolic sodium methoxide, giving A-[(2-hydroxyethyl) thio]-3,4-dimethoxy-benzeneacetonitrile 5, which is dissolved in dimethyl sulfoxide under an inert atmosphere and reacted first with sodium hydride, then with R-Y, where R is $C_{1-6}$ alkyl or aryl, and Y is bromo, chloro or iodo, giving A-[(2-hydroxyethyl) thio]-3,4-dimethoxy-A-substituted benzeneacetonitrile 6. Preferably, Y is bromo. If it is desired that R be hydrogen in the final product, then the reaction of 5 with sodium hydride and R-Y is omitted. Compound 6 (or compound 5 where R is hydrogen) is reacted with R'-X. R'-X is a compound where X is a leaving or displacing group. Examples of X include chloro, bromo, iodo, tosyl, as well as other conventional such groups. R' may be any appropriate group which can accept the hydroxyl group or hydrogen of 5 or 6 when the leaving group X is bound to 5 or 6. For example, when X is cloro, bromo or iodo, R' may be SO, giving $SOCl_2$, $SOBr_2$ or $SOI_2$, respectively. When X is tosyl, R' may be chloro.

Thus, compound 6 is reacted with R'-X, giving A-[(2-X-ethyl) thio]-3,4-dimethoxy-A-substituted benzeneacetonitrile 7, which is then reacted with 3,4-dimethoxyphenylethyl-N-methylamine in dry dimethylformamide, giving the desired compounds 8, in the base form, which is converted to a pharmaceutically acceptable salt by conventional means. Examples of such salts include chloride, bromide, sulfate and fumarate. In a preferred embodiment, 8 is converted to the monohydrochloride salt by reaction with ethereal hydrochloric acid.

The compounds of this invention may be combined with one or more conventional pharmaceutically acceptable carriers, such as solvents, diluents, and the like, and may be administered orally in such forms as tablets, capsules, dispersible powders, granules or suspensions, or parenterally in the form of sterile injectable solutions or suspensions.

The utility of certain compounds of this invention was established in the following tests.

CALCIUM ANTAGONIST TESTS

Test 1

Male Sprague-Dawley rats, weighing 300–470 g, were killed and their thoracic aortae were removed immediately, cleared of blood, fat and connective tissue and cut into rings 1-2 mm wide. The rings were cannulated with a pair of triangle-shaped stainless steel rods and suspended in 10 milliliter organ baths containing Krebs solution (112.9 mM sodium chloride; 4.7 mM potassium chloride; 1.2 mM potassium dihydrogen phosphate; 1.2 mM magnesium sulfate heptahydrate; 25.0 mM sodium bicarbonate; 11.5 mM dextrose; and 1.8 mM calcium chloride dihydrate). The bath media was maintained at 37° C. and aerated with 5% carbon dioxide in oxygen.

At the start of the test, the aortic rings were stretched to an initial tension of one gram. The tissues were then allowed to equilibrate for 90 minutes until they reached a steady tension. Changes in tension were recorded using a force displacement transducer coupled to a Grass polygraph.

Following the period of equilibration, 200 Ml of 2.5 M potassium chloride were added to each bath to make a final bath concentration of 50 mM. The potassium chloride-induced contractions were repeated until a constant tension was obtained. These initial contractions served as a control for subsequent contractions induced in the presence of a test compound.

Three compounds were tested: (1) A-[[2-[[2-(3,4dimethoxyphenyl)ethyl]methylamino]ethyl]thio]-3,4-dimethoxy-A-(1-methylethyl) benzeneacetonitrile monohydrochloride (R=1-methylethyl), (2) A-[[2-[[2(3,4-dimethoxyphenyl)ethyl]methylamino]ethyl]thio]-3,4-dimethoxy-A-benzeneacetonitrile monohydrochloride (R=hydrogen), and (3) Verapamil. Each compound was dissolved in ethanol to a stock concentration of $10^{-2}$ M. The ability of these compounds to inhibit a potassium chloride-induced contraction was determined by comparing the tension developed in the presence of each compound versus the control.

A compound was considered active if it inhibited greater than 50% of the contraction at a bath concentration of $3 \times 10^{-5}$ M. The 1-methylethyl substituted thio compound of this invention inhibited more than 50% of the contraction at a bath concentration of $8 \times 10^{-7}$ M. This was comparable to and was within experimental error of the value of $1 \times 10^{-8}$ M for Verapamil. The unsubstituted thio compound of this invention was also active, inhibiting more than 50% of the contraction at a bath concentration of $3 \times 10^{-6}$ M.

Test 2

Antihypertensive activity was measured in the rat by the mean arterial blood pressure (MABP) in millimeters of mercury and heart rate (HR) in beats per minute (average two rats). Verapamil at a dose of 50 mg/kg showed MABP and HR values of 93 and 350, respectively, while the 1-methylethyl substituted thio compound at a dose of 100 mg/kg showed MABP and HR values of 97 and 320, respectively. Thus, the two compounds demonstrated comparable antihypertensive activity in this test.

Test 3

Antihypertensive activity was also measured in renal hypertensive dogs. Verapamil at a dose of 10 mg/kg caused a 30 millimeters of mercury drop in blood pressure over a four hour period with an increase in HR of 75, while the 1-methylethyl substituted thio compound at a dose of 20 mg/kg caused a 45 millimeter drop over a two hour period and an increase in HR to above 153.

Tests 4 & 5

The same two compounds were also tested for coronary vasodilation in the Langendorff isolated rat heart model as measured by the drop in perfusion pressure upon administering each compound by bolus injection and anti-ischemic activity as measured by their ability to prevent isoproteranol-induced myocardial infarction in rats. The two compounds were comparably active.

The invention is further described in the following examples.

EXAMPLE 1

Synthesis of A-[[2-[2-(3,4-dimethoxyphenyl)ethyl]methylamino]ethyl]thio]-3,4-dimethoxy-A-(1-methylethyl) benzeneacetonitrile, monohydrochloride (a) Preparation of 3,4-dimethoxyphenyl-A-chloroacetonitrile To a solution of 37.7 grams of 3,4-dimethoxybenzaldehyde and 25 grams of trimethylsilylcyanide in 100 milliliters of dichloromethane at room temperature were added 100 milligrams of zinc iodide. Swirling produced a strong exotherm, which was moderated by cooling in ice water. After 2 hours at room temperature, the excess dichloromethane was evaporated. The residue was poured into 800 milliliters of 3N hydrochloric acid, stirred vigorously for 30 minutes and the resulting solid collected. This solid was dissolved in 800 milliliters of dichloromethane and stirred while 22.5 grams of thionyl chloride were added rapidly over a 30 second period. The resulting solution was stirred for 24 hours and then shaken with ice water. The organic phase was separated, dried and evaporated in vacuo with minimal heating. After standing overnight, the liquid residue was dissolved in ether, filtered and the filtrate evaporated, giving 27 grams of the desired compound as a dark viscous liquid.

(b) Preparation of A-[(2-hydroxyethyl)thio]-3,4-dimethoxybenzeneacetonitrile

A solution of 10 grams of 2-mercaptoethanol in 128 milliliters of 1N methanolic sodium methoxide was added to a stirred solution of 27 grams of 3,4-dimethoxyphenyl-A-chloroacetonitrile in 125 milliliters of methanol, producing a mild exotherm. After stirring 10 minutes, the mixture was poured into water. The oil which separated was extracted into ether which was dried and evaporated, giving 23.6 grams of the desired compound as a dark orange viscous oil.

(c) Preparation of A-[(2-chloroethyl)thio]-3,4-dimethoxy-A-(1-methylethyl) benzeneacetonitrile To a solution of 10.4 grams of A-[(2-hydroxyethyl)thio]-3,4-dimethoxybenzeneacetonitrile in 80 milliliters of dry dimethyl sulfoxide under nitrogen was added 2 grams of 50% sodium hydride in mineral oil, with continual nitrogen passage. After stirring 10 minutes, the mixture was cooled in ice water and 5.6 grams of isopropyl bromide was added during 1 to 2 minutes. The reaction was then stirred at room temperature for 30 minutes, then cautiously poured into ice water. The aqueous mixture was extracted with ether and the extract dried and evaporated, giving 11.4 grams of A-[(2-hydroxyethyl) thio]-3,4-dimethoxy-A-(1-methylethyl) benzeneacetonitrile as a dark orange viscous oil.

A stirred solution of 5.7 grams of the above compound in 100 milliliters of dichloromethane was treated with 1.4 milliliters of thionyl chloride. The mixture was stirred overnight, then poured into ice-water, and thoroughly shaken. The organic phase was separated, dried and evaporated giving an oil which was purified by thick-layer chromatography, giving 3.1 grams of the desired compound as a viscous yellow oil.

(d) Preparation of A-[[2-[[2-(3,4-dimethoxyphenyl)ethyl]methylamino]ethyl]thio]-3,4-dimethoxy-A-(1-methylethyl) benzeneacetonitrile, monohydrochloride To a mixture of 3.1 grams of A-[(2-chloroethyl) thio]-3,4-dimethoxy-A-(1-methylethyl) benzeneacetonitrile and 4.5 grams of 3,4-dimethoxyphenylethyl-N-methylamine was added 20 milliliters of dry dimethylformamide. The mixture was stirred and heated at 90°–95° C. for 24 hours and then poured into ice water. After 30 minutes, the aqueous phase was decanted and the gummy residue washed with water, then dissolved in ether. The ether solution was dried and evaporated to a dark orange viscous oil which was purified by thick-layer chromatography, giving 1.7 grams of the base form of the desired product as a viscous orange oil.

This oil was dissolved in 400 milliliters of ether, treated with an excess of ethereal hydrochloric acid and stirred for 20 minutes. The ethereal supernatant was decanted, the residue washed with ether and then stirred with ether for 3 days. The solid was collected, triturated with acetone, collected, washed with ether and dried, giving 1.25 grams of the desired product, which had a melting point of 125°–131° C.

EXAMPLE 2

Synthesis of A-[[2-[[2-(3,4-dimethoxyphenyl)ethyl]methylamino]ethyl]thio]-3,4-dimethoxybenzeneacetonitrile. monohydrochloride (a) Preparation of 3-4-dimethoxyphenyl-A-chloroacetonitrile The procedure of step (a) of Example 1 was repeated to obtain 27 grams of the desired compound.

(b) Preparation of A-[(2-hydroxyethyl)thio]-3,4-dimethoxybenzeneacetonitrile

The procedure of step (b) of Example 1 was repeated to obtain 23 grams of the desired compound.

(c) Preparation of A-[(2-tosyloxyethyl)thio]-3,4-dimethoxybenzeneacetonitrile

A stirred solution of 1.4 grams of A-[(2-hydroxyethyl) thio]-3,4-dimethoxybenzeneacetonitrile in 12 milliliters of dry pyridine was treated with 1.2 grams of tosyl chloride at room temperature. The resulting mixture was stirred at room temperature for 3 hours, then poured into ice-water. An orange gum formed. The aqueous phase was decanted and the residue washed with water, then dissolved in ether. The ethereal extract was dried and evaporated. The extract was purified by thin-layer chromatography, giving 1.2 grams of the desired compound as an orange, very viscous oil.

(d) Preparation of A-[[2-[[2-(3,4-dimethoxyphenyl)ethyl]methylamino]ethyl]thio]-3,4-dimethoxybenzeneacetonitrile, monohydrochloride A solution of 1.5 grams of 3,4-dimethoxyphenylethyl-N-methylamine in 5 milliliters of dry dimethyl formamide was added to 1.1 grams of A-[(2-tosyloxyethyl)thio]-3,4-dimethoxybenzeneacetonitrile at room temperature. The resulting solution was kept at room temperature for 18.5 hours. A large excess of ice-water was then added. A yellow orange gum formed. The aqueous phase was decanted, the residue washed with water, then dissolved in ether. The ether solution was dried and evaporated. The extract was purified by thick-layer chromatography, giving 0.25 grams of the desired compound as an orange-yellow, viscous oil. A portion of this oil was redissolved in ether and the ethereal solution treated with an excess of gaseous hydrochloric acid. A light brown gummy material separated. The ethereal phase was decanted and the product washed repeatedly with fresh ether, then stirred in ether overnight and dried, giving the desired product as a colorless solid, which had a melting point of 131°–137° C.

We claim:

1. A compound having the formula

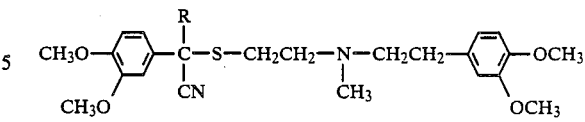

where R is hydrogen, $C_{1-6}$ alkyl or phenyl, and pharmaceutically acceptable salts thereof.

2. A compound according to claim 1 wherein the pharmaceutically acceptable salt is monohydrochloride.

3. A compound according to claim 2 wherein R is $-CH-(CH_3)_2$.

4. A compound according to claim 2 wherein R is hydrogen.

5. A method of blocking the calcium channel in mammals which comprises administering to such mammal an effective amount of a compound of claim 1.

6. A therapeutic composition of matter useful for blocking the calcium channel in mammals which comprises an amount of a compound of claim 1 effective therefor in association with a pharmaceutically effective carrier.

* * * * *